United States Patent
Venkatachalam et al.

(10) Patent No.: US 11,052,049 B2
(45) Date of Patent: Jul. 6, 2021

(54) CAPSULE DOSAGE FORMS OF TRIAMTERENE, AND PROCESS OF PREPARATION THEREOF

(71) Applicant: ATOZ PHARMACEUTICALS PVT LTD, Chennai (IN)

(72) Inventors: Natarajan Venkatachalam, Chennai (IN); Olaganathan Arumugam, Chennai (IN)

(73) Assignee: ATOZ PHARMACEUTICALS PVT LTD, Chennai (IN)

( * ) Notice: Subject to any disclaimer, the term of this patent is extended or adjusted under 35 U.S.C. 154(b) by 0 days.

(21) Appl. No.: 16/844,802

(22) Filed: Apr. 9, 2020

(65) Prior Publication Data
US 2020/0323783 A1     Oct. 15, 2020

(30) Foreign Application Priority Data

Apr. 11, 2019   (IN) .............................. 201941014707

(51) Int. Cl.
*A61K 9/48*     (2006.01)
*A61K 31/519*   (2006.01)

(52) U.S. Cl.
CPC .......... *A61K 9/4858* (2013.01); *A61K 31/519* (2013.01)

(58) Field of Classification Search
None
See application file for complete search history.

(56) References Cited

U.S. PATENT DOCUMENTS

| 4,255,413 A * | 3/1981 | Rattie ................... A61K 9/485 424/452 |
| 4,517,179 A * | 5/1985 | Raghunathan ....... A61K 9/2009 514/249 |
| 4,681,765 A * | 7/1987 | Guley ................. A61K 9/4841 424/455 |

\* cited by examiner

*Primary Examiner* — Brian J Davis

(57) ABSTRACT

The present disclosure provides for a capsule dosage form of triamterene, the dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent having a weight percentage in a range of 42-73.5% with respect to the total mixture/ingredients encapsulated in the capsule dosage form. The present disclosure also provides for a convenient process for preparation of the capsule dosage form.

7 Claims, No Drawings

CAPSULE DOSAGE FORMS OF TRIAMTERENE, AND PROCESS OF PREPARATION THEREOF

FIELD OF THE INVENTION

The present invention relates to the field of capsule dosage forms of triamterene. The present disclosure also provides for a convenient process of preparation of the capsule dosage forms of triamterene the present Application. The present is based on, and claims priority from an Indian Application Number 201941014707 filed on 11 Apr. 2019, the disclosure of which is hereby incorporated by reference herein

BACKGROUND

Triamterene (trade name Dyrenium) is a potassium-sparing diuretic, generally used in combination with other drugs, for treatment of hypertension and edema. The drug is widely used, particularly for its ability to restrict the loss of potassium caused by other diuretics. Conventionally, gelatin capsule dosage units comprising triamterene and triamterene hydrochlorothiazide are known (Chem. Abs. 1967, No. 111345).

Generally, the formulation of triamterene in capsule forms is extremely challenging. Owing to its poor solubility and low dose of the medicament, it is often necessary to add several excipients such as fillers, glidants, diluents, and surfactants to bulk up the formulation. For example, U.S. Pat. Nos. 4,681,765 and 4,255,413 discloses a gelatin capsule dosage form containing triamterene, 2, 4, 7-triamino-6-phenylpteridine, which results in rapid dissolution of the active ingredient. The dosage form comprises the pharmaceutical binder methylcellulose in combination with low doses of a surfactant or a carbonate salt as disintegrants.

U.S. Pat. No. 4,517,179 discloses a rapidly dissolving uniform compositions of low water solubility drugs formed from a dry mixture of the drug having a reduced particle size (triamterene) in combination with properly selected and sized excipients including microcrystalline cellulose, dibasic calcium phosphate, starches and a lubricant. However, a disadvantage is that these excipients interfere with the release of the medicament. Also, the process steps adopted to prepare the conventional capsule dosage forms of triamterene result in high bioavailability of triamterene in the plasma. Further, it could potentially cause several side effects such as hyperkalemia. Therefore, there exists a need to develop a cost-effective, convenient process of preparation of capsule dosage forms of triamterene that lower the bioavailability of triamterene in plasma, and at the same time offers a therapeutic efficacy bioequivalent to the product that are currently available in the market (e.g. Dyrenium).

The above information is presented as background information only to help the reader to understand the present invention. Applicants have made no determination and make no assertion as to whether any of the above might be applicable as prior art with regard to the present application.

OBJECT OF THE INVENTION

The principal object of the embodiments herein is to provide for capsule dosage forms of triamterene.

Another object of the present disclosure provides for capsule dosage forms of triamterene with a therapeutic efficacy comparable or bioequivalent to the conventional dosage forms of triamterene that are available in the market.

Yet another object of the invention is to provide a convenient cost-effective composition and process for preparation of capsule dosage forms of triamterene.

SUMMARY

Accordingly, the invention provides a capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent selected from a group consisting of lactose, or hydrates thereof, sugar alcohols, and/or combinations thereof having a weight percentage in a range of 42-73.5% with respect to the total ingredients in the capsule dosage form.

In another aspect of the present disclosure, there is provided a process for preparation of capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent selected from a group consisting of lactose, or hydrates thereof, sugar alcohols, and/or combinations thereof having a weight percentage in a range of 42-73.5% with respect to the ingredients in the capsule dosage form; said process comprising: i) blending triamterene and magnesium stearate for a period of 8-12 minutes at 10-20 rpm to obtain a first mixture; and ii) contacting the first mixture with diluent for a period of 8-12 minutes at 10-20 rpm to obtain a second mixture; c) optionally compressing the second mixture to obtain a tablet; and d) encapsulating the second mixture or the tablet into a capsule to obtain the capsule dosage form of triamterene.

These and other aspects of the embodiments herein will be better appreciated and understood when considered in conjunction with the following description. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF INVENTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. Also, the various embodiments described herein are not necessarily mutually exclusive, as some embodiments can be combined with one or more other embodiments to form new embodiments. The term "or" as used herein, refers to a non-exclusive or, unless otherwise indicated. The examples used herein are intended merely to facilitate an understanding of ways in which the embodiments herein can be practiced and to further enable those skilled in the art to practice the embodiments herein. Accordingly, the examples should not be construed as limiting the scope of the embodiments herein.

Conventionally used compositions of triamterene are mixed with several excipients including surfactants and glidants to impart desirable properties to the composition and to bulk up the composition. Therefore, the objective of the present invention is to provide a composition and the process that shall lower the bioavailability of triamterene molecule. The other objective of the present invention is to produce the product bioequivalent in comparison to the product currently used in the market like Dyrenium, without the excipients such as surfactant, wetting agents, flow enhancers or glidants, etc.

In an embodiment of the present disclosure, there is provided a capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent selected from a group consisting of lactose, or hydrates thereof, sugar alcohols, and/or combinations thereof having a weight percentage in a range of 42-73.5% with respect to the ingredients in the capsule dosage form. In another embodiment, the diluent is lactose monohydrate.

In another embodiment, the capsule dosage form comprising: a) triamterene having a weight percentage of 37.04% with respect to the total ingredients in the capsule dosage form; b) magnesium stearate having a weight percentage of 5.19% with respect to the total ingredients in the capsule dosage form; and c) lactose monohydrate having a weight percentage of 57.78% with respect to the ingredients in the capsule dosage form.

In an embodiment of the present disclosure, there is provided a capsule dosage form as described herein, wherein the capsule dosage form contains about 5 mg to 100 mg of triamterene. In another embodiment of the present disclosure, the capsule dosage form contains about 50 mg to 100 mg of triamterene.

In an embodiment of the present disclosure, the capsule dosage form may optionally contain one or more actives in addition to triamterene. For example, the capsule dosage form may also contain hydrochlorothiazide in addition to triamterene.

In an embodiment of the present disclosure, the release profile of triamterene is in the range of 45-60% within 15 minutes in invitro condition. In another embodiment, the drug dissolved is greater than 75% in 60 minutes in invitro condition. In an example, the in vitro release profile studies were carried out in 900 ml of 0.1N acetic acid media using USP Apparatus 2.

In an embodiment of the present disclosure, there is provided a process for preparation of capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent selected from a group consisting of lactose, or hydrates thereof, sugar alcohols, and/or combinations thereof having a weight percentage in a range of 42-73.5% with respect to the ingredients in the capsule dosage form; said process comprising: i) blending triamterene and magnesium stearate for a period of 8-12 minutes at 10-20 rpm to obtain a first mixture; and ii) contacting the first mixture with the diluent for a period of 8-12 minutes at 10-20 rpm to obtain a second mixture; c) optionally compressing the second mixture to obtain a tablet; and d) encapsulating the second mixture or the tablet into a capsule to obtain the capsule dosage form of triamterene. In an embodiment of the present disclosure, the second mixture or the tablet is encapsulated into a hard gelatin capsule of size 2 to encapsulate 100 mg of triamterene; and size 4 to encapsulate 50 mg of triamterene.

In another embodiment, the process comprises the steps of: i) blending triamterene and magnesium stearate for a period of 10 minutes at 15 rpm to obtain a first mixture; and ii) contacting the first mixture with at least one diluent selected from a group consisting of lactose, or hydrates thereof, sugar alcohols, and/or combinations thereof for a period of 10 minutes at 15 rpm to obtain a second mixture; iii) optionally compressing the second mixture to obtain a tablet; and iv) encapsulating the second mixture or the tablet into a capsule to obtain the capsule dosage form of triamterene. In an embodiment, the blending of triamterene with magnesium stearate and/or the first mixture with the diluent is performed in a blender.

In an embodiment of the present disclosure, there is provided a process as described herein, wherein the triamterene, magnesium stearate, and the diluent are sieved through a #40 mesh screen prior to the blending.

In an embodiment of the present disclosure, there is provided a process for preparation of capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) at least one diluent selected from a group consisting of lactose, or hydrates thereof, sugar alcohols, and/or combinations thereof having a weight percentage in a range of 42-73.5% with respect to the ingredients in the capsule dosage form; said process comprising: i) sieving triamterene, magnesium stearate, and the diluent through a #40 mesh screen; ii) blending triamterene and magnesium stearate, generated in step (i) for a period of 8-12 minutes at 10-20 rpm to obtain a first mixture; and iii) contacting the first mixture with the diluent (obtained in step i) for a period of 8-12 minutes at 10-20 rpm to obtain a second mixture; iv) optionally compressing the second mixture to obtain a tablet; and v) encapsulating the second mixture or the tablet into a capsule to obtain the capsule dosage form of triamterene.

In an embodiment of the present disclosure, there is provided a process as described herein, wherein the process is performed under anhydrous conditions. The term "anhydrous", refers to absence of water.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

EXAMPLES

The disclosure will now be illustrated with working examples, which is intended to illustrate the working of disclosure not intended to take restrictively to imply any limitations on the scope of the present disclosure. Unless defined otherwise, all technical and scientific terms used herein have the same meaning as commonly understood to any one of the ordinary skilled in the art to which this disclosure belongs. Although methods and materials similar or equivalent to those described herein can be used in the practice of disclosed methods and compositions, the exemplary methods, devices and materials are described herein. It is to be understood that this disclosure is not limited to particular methods, and experimental conditions described, as such methods and conditions may apply.

The examples described herein clearly depict the effect of magnesium stearate, sodium lauryl sulfate (SLS), and colloidal silicon dioxide on the effect of dissolution release profile of triamterene. SLS and colloidal silicon dioxide are commonly used as surfactants, and glidants in formulations of triamterene. The working examples clearly depict that the capsule dosage forms prepared through the process steps of the present disclosure obviate the need for use of any surfactants or glidants, and the same has been experimentally established. Accordingly, the present disclosure provides for a process for preparation of capsule dosage form comprising: a) triamterene having a weight percentage in a range of 25-45% with respect to the total ingredients in the capsule dosage form; b) magnesium stearate having a weight percentage in a range of 1.5-13% with respect to the total ingredients in the capsule dosage form; and c) lactose monohydrate having a weight percentage in a range of 42-73.5% with respect to the ingredients in the capsule dosage form; said process comprising: i) blending triamterene and magnesium stearate for a period of 8-12 minutes at 10-20 rpm to obtain a first mixture; and ii) contacting the first mixture with lactose monohydrate for a period of 8-12 minutes at 10-20 rpm to obtain a second mixture; c) optionally compressing the second mixture to obtain a tablet; and d) encapsulating the second mixture or the tablet into a capsule to obtain the capsule dosage form of triamterene.

The capsule dosage forms prepared through the process of the present disclosure impart reduced bioavailability to triamterene composition prepared by conventional process, but a therapeutic efficacy comparable to the currently marketed drugs like Dyrenium, without necessitating the need for use of any surfactants or wetting agents, or glidants This is because Magnesium stearate when blended at 140-160 rpm results in formation of a film on the active ingredient triamterene, thereby retarding the faster dissolution of triamterene in invitro.

Example 1—Effect of Magnesium Stearate on Drug (Triamterene) Release

In order to evaluate the effect of magnesium stearate on the dissolution properties of triamterene, six different capsule dosage forms of triamterene (1-6), with varying weight percentage of magnesium stearate ranging from 1.90-7.40% have been prepared by mixing all the ingredients as provided below in Table 1.

TABLE 1

| Ingredients | 1 | 2 | 3 | 4 | 5 | 6 |
|---|---|---|---|---|---|---|
| Triamterene | 37.04 | 37.04 | 37.04 | 37.04 | 37.04 | 37.04 |
| Lactose Monohydrate | 58.06 | 56.26 | 55.36 | 54.76 | 54.36 | 52.56 |
| Sodium Lauryl Sulphate | 2.00 | 2.00 | 2.00 | 2.00 | 2.00 | 2.00 |

TABLE 1-continued

| Ingredients | 1 | 2 | 3 | 4 | 5 | 6 |
|---|---|---|---|---|---|---|
| Magnesium Stearate | 1.90 | 3.70 | 4.60 | 5.20 | 5.60 | 7.40 |
| Colloidal Silicon dioxide | 1.00 | 1.00 | 1.00 | 1.00 | 1.00 | 1.00 |

The percentage release of triamterene, for all the 6 capsule dosage forms, was measured at various time intervals, along with content uniformity and blend uniformity, the results of which are presented below in Table 2.

TABLE 2

| Time (min) | 1 | 2 | 3 | 4 | 5 | 6 |
|---|---|---|---|---|---|---|
| 15 | 76.88 | 54.54 | 45.19 | 51.20 | 41.73 | 46.49 |
| 30 | 94.72 | 73.93 | 65.07 | 59.55 | 55.36 | 58.99 |
| 45 | 102.47 | 78.94 | 70.70 | 79.19 | 53.24 | 66.80 |
| 60 | 102.68 | 85.00 | 80.66 | 87.00 | 69.29 | 66.69 |
| 90 | 106.72 | 90.79 | 85.72 | 92.44 | 76.54 | 75.79 |
| 120 | 105.90 | 89.43 | 92.86 | 94.42 | 80.29 | 84.40 |
| Blend Uniformity | | | | | | |
| Mean | 92.85 | 95.69 | 94.19 | 102.31 | 98.51 | 98.56 |
| RSD | 8.32 | 3.69 | 3.92 | 3.40 | 6.54 | 4.50 |
| Content Uniformity | | | | | | |
| Mean | 101.75 | 98.35 | 95.42 | 91.04 | 98.72 | 108.94 |
| RSD | 0.49 | 0.90 | 1.77 | 3.94 | 0.64 | 5.91 |

From the Table 2 it can be inferred that the rate of dissolution of triamterene was found to be much lower with increasing concentrations of magnesium stearate. This is because magnesium stearate can form films on surface of active triamterene during prolonged mixing, leading to a reduction in percentage of triamterene dissolves at $15^{th}$ min (based on the amount of magnesium stearate used) during dissolution study.

Example 2: Process for Preparing the Capsule Dosage Forms

The process of preparing the six capsule dosage forms comprises the steps of: a) sieving/deagglomeration of triamterene (optional), lactose monohydrate, magnesium stearate, and optionally sodium lauryl sulphate, and colloidal silicon dioxide through a 40 #mesh screen; b) blending triamterene, magnesium stearate; and optionally sodium lauryl sulphate for 10 minutes at 15 rpm to obtain a first mixture; c) contacting the first mixture with lactose monohydrate and optionally colloidal silicon dioxide for a period of 10 minutes at 15 rpm to obtain a second mixture; and d) encapsulating the second mixture within a hard gelatin capsule to obtain the capsule dosage forms of triamterene.

Example 3: Effect of Sodium Lauryl Sulfate (SLS) on Drug (Triamterene) Release SLS is a commonly used as a surfactant in many pharmaceutical formulations. The dissolution release profile of formulations processed with and without sodium lauryl sulphate concentrations (7 and 8) have been studied, and the results of which are presented below in Table 3.

TABLE 3

| | 7 | 8 |
|---|---|---|
| Ingredients | | |
| Triamterene | 37.04 | 37.04 |
| Lactose Monohydrate | 54.78 | 56.78 |
| Sodium Lauryl Sulphate | 2.00 | 0.00 |
| Magnesium Stearate | 5.19 | 5.19 |
| Colloidal Silicon Dioxide | 1.00 | 1.00 |
| % release of triamterene | | |
| Time in Mins | | |
| 15 | 42 | 44 |
| 30 | 66 | 70 |
| 45 | 74 | 81 |
| 60 | 77 | 87 |
| 90 | 87 | 94 |
| 120 | 92 | 97 |

From the data provided in Table 3, it can be inferred that the drug (triamterene) release profiles are very similar for the formulations processed with and without the surfactant (SLS). In other words, it can be concluded that the presence or absence of SLS in the formulation does not markedly impact the drug release profile.

Example 4: Effect of Silicon Dioxide on Drug (Triamterene) Release

Silicon dioxide is a commonly used as a glidant in many pharmaceutical formulations to improve the flowability properties in a formulation. The dissolution release profile of formulations processed with and without silicon dioxide (9 and 10) have been studied, and the results of which are presented below in Table 4.

TABLE 4

| | 9 | 10 |
|---|---|---|
| Ingredients | | |
| Triamterene | 37.04 | 37.04 |
| Lactose Monohydrate | 56.78 | 57.78 |
| Magnesium Stearate | 5.19 | 5.19 |
| Colloidal Silicon Dioxide | 1.00 | 0.00 |
| Total | 100.00 | 100.00 |
| % release of triamterene | | |
| Time in Mins | | |
| 15 | 44 | 61 |
| 30 | 70 | 83 |
| 45 | 81 | 88 |
| 60 | 87 | 91 |
| 90 | 94 | 93 |
| 120 | 97 | 95 |
| Bulk Density | 0.47 | 0.51 |
| Tapped Density | 0.73 | 0.83 |
| Compressibility Index | 36.02 | 37.92 |
| Hausner Ratio | 1.56 | 1.61 |
| Angle of Repose | 43.21 | 44.05 |

The percentage of drug release was found to be lower in compositions comprising silicon dioxide for the first 30 minutes. However, the release profiles are not very markedly different after the 30 minutes. Also, from the Table 4 it can be inferred that the Hausner ratio, and the angle of repose, both of which are indicative of flowability of a powder, are found to be comparable in formulations with and without silicon dioxide. The data suggests that the use of silicon dioxide is not very crucial to the capsule dosage forms of the present invention.

Advantages of the Present Disclosure

The present disclosure provides a process for preparation of capsule dosage form comprising: i) blending triamterene and magnesium stearate for a period of 8-12 minutes at 10-20 rpm to obtain a first mixture; and ii) contacting the first mixture with lactose monohydrate for a period of 8-12 minutes at 10-20 rpm to obtain a second mixture; iii) optionally compressing the second mixture to obtain a tablet; and iv) encapsulating the second mixture or the tablet into a capsule to obtain the capsule dosage form of triamterene. The capsule dosage forms prepared through the process of the present disclosure impart reduced bioavailability but a therapeutic efficacy comparable to the currently marketed product like Dyrenium, without necessitating the need for use of any surfactants or wetting agents, or glidants. This is because Magnesium stearate when blended at 80-240 revolutions results in formation of a film on the triamterene (active powder), thereby retarding the release of the triamterene.

We claim:

1. A capsule dosage form comprising:
    a) triamterene having a weight percentage in a range of 35-40% with respect to the total ingredients in the capsule dosage form;
    b) magnesium stearate having a weight percentage in a range of 1.5-5.5% with respect to the total ingredients in the capsule dosage form; and
    c) at least one diluent having a weight percentage in a range of 50-60% with respect to the total mixture/ingredients encapsulated in the capsule dosage form
        wherein the in vitro release of triamterene is in the range of 45-60% at $15^{th}$ minute and not less than 75% at $60^{th}$ minute in acidic conditions.

2. The capsule dosage form as claimed in claim 1, wherein the at least one diluent is at least one selected from a group consisting of lactose, or hydrates thereof, sugar alcohols, and combinations thereof.

3. The capsule dosage form as claimed in claim 1, contains about 5 mg to 100 mg of triamterene.

4. A process for preparing a capsule dosage form, said process comprises:
    i) blending triamterene and magnesium stearate for a period of 8-12 minutes at 10-20 rpm to obtain a first mixture; and
    ii) contacting the first mixture with at least one diluent selected from a group consisting of lactose, or hydrates thereof, sugar alcohols, and/or combinations thereof, for a period of 8-12 minutes at 10-20 rpm to obtain a second mixture;
    iii) optionally compressing the second mixture to obtain a tablet; and
    iv) encapsulating the second mixture or the tablet into a capsule to obtain the capsule dosage form of triamterene,
        wherein the in vitro release of triamterene is in the range of 45-60% at $15^{th}$ minute and not less than 75% at $60^{th}$ minute in acidic conditions.

5. The process for preparing the capsule dosage form as claimed in claim 4,
    wherein the triamterene, magnesium stearate, and the diluent are sieved through a #40 mesh screen prior to the blending.

6. The process for preparing the capsule dosage form as claimed in claim 4, wherein the diluent is lactose monohydrate.

7. The process for preparing the capsule dosage form as claimed in claim 4, wherein the processing is performed under anhydrous conditions.

* * * * *